United States Patent
Aufrichtig et al.

(10) Patent No.: US 6,359,961 B1
(45) Date of Patent: Mar. 19, 2002

(54) APPARATUS AND METHODS FOR STEREO RADIOGRAPHY INCLUDING REMOTE CONTROL VIA A NETWORK

(75) Inventors: Richard Aufrichtig, Mountain View, CA (US); Jeffrey A. Kautzer, Waukesha, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/473,283

(22) Filed: Dec. 28, 1999

Related U.S. Application Data

(63) Continuation-in-part of application No. 09/268,788, filed on Mar. 16, 1999, now Pat. No. 6,256,372.

(51) Int. Cl.[7] .............................................. A61B 6/02
(52) U.S. Cl. ......................... 378/41; 378/62; 378/98.2
(58) Field of Search ............................... 378/4, 41, 62, 378/63, 98, 98.2, 901

(56) References Cited

U.S. PATENT DOCUMENTS

| | | | | | |
|---|---|---|---|---|---|
| 4,748,511 A | * | 5/1988 | Nichols et al. | ............. | 358/433 |
| 4,853,946 A | * | 8/1989 | Elliott et al. | ................... | 378/4 |
| 5,400,387 A | * | 3/1995 | Gard et al. | ................. | 378/207 |
| 5,434,900 A | * | 7/1995 | Tanaka et al. | ................. | 378/15 |
| 5,482,043 A | * | 1/1996 | Zulauf | ........................ | 600/437 |
| 5,692,029 A | * | 11/1997 | Husseiny et al. | ............. | 378/88 |
| 5,737,382 A | * | 4/1998 | Stierstorfer | .................. | 378/19 |
| 5,754,785 A | * | 5/1998 | Lysik et al. | ................. | 709/222 |
| 6,005,911 A | * | 12/1999 | Cheung | ........................ | 378/37 |
| 6,084,939 A | * | 7/2000 | Tamura | ..................... | 378/98.2 |
| 6,091,982 A | * | 7/2000 | Reinke et al. | ............. | 600/407 |
| 6,097,785 A | * | 8/2000 | Elam | ........................... | 378/45 |
| 6,178,225 B1 | * | 1/2001 | Zur et al. | .................. | 378/98.2 |
| 6,200,025 B1 | * | 3/2001 | Rich | .......................... | 378/207 |
| 6,205,199 B1 | * | 3/2001 | Polichar et al. | ............ | 378/98.8 |
| 6,212,256 B1 | * | 4/2001 | Miesbauer et al. | ........ | 378/118 |
| 6,230,043 B1 | * | 5/2001 | Johnson | ...................... | 600/425 |
| 6,256,372 B1 | * | 7/2001 | Aufrichtig et al. | ........... | 378/41 |

\* cited by examiner

*Primary Examiner*—Robert H. Kim
*Assistant Examiner*—Allen C. Ho
(74) *Attorney, Agent, or Firm*—Foley & Lardner; Peter J. Vogel; Michael A. Della Penna

(57) ABSTRACT

A radiographic imaging system includes an X-ray emitter, an X-ray detector, and a network. The X-ray emitter is actuatable to emit an X-ray beam centered about an X-ray beam axis. The X-ray detector has a generally planar configuration and is situated within the path of the X-ray beam to thereby generate an image when the X-ray detector receives the X-ray beam. The network couples at least one of the X-ray emitter and X-ray detector to a remote facility. The network provides the X-ray emitter and the X-ray detector with remote services from the remote facility. A corresponding method is also provided.

20 Claims, 5 Drawing Sheets

APPARATUS AND METHODS FOR STEREO RADIOGRAPHY INCLUDING REMOTE CONTROL VIA A NETWORK

CROSS-REFERENCE TO RELATED APPLICATIONS

This application is a continuation-in-part (CIP) of U.S. application Ser. No. 09/268,788, entitled "Apparata And Methods For Stereo Radiography" by Richard Aufrichtig et al. filed on Mar. 16, 1999, now U.S. Pat. No. 6,256,372.

BACKGROUND OF THE INVENTION

The present invention relates generally to the field of medical diagnostic systems, such as imaging systems. More particularly, the invention relates to a system and technique for stereo radiography including remote control over a network.

The classic radiographic or "X-ray" image is obtained by situating an object to be imaged between an X-ray emitter (i.e., an X-ray tube) and an X-ray detector. Emitted X-rays pass through the object to strike the detector, with the response of the detector varying over its area as a function of the intensity of the incident X-rays. Since the intensity of the X-rays incident on the detector is largely a function of the density of the object along the path of the X-rays, the detector receives a shadow image of the object which may then be viewed and analyzed by X-ray technicians, e.g., radiologists. In the case of analog radiographic systems, the detector is formed of X-ray film, whereas digital radiographic systems have solid-state detector components (e.g., scintillator/photodiode arrays) whereby the image is provided in electronic form.

One difficulty which is commonly encountered with the analysis of radiographic images is the proper identification of objects contained within the image. As an example, the identification of organs and other body structures is particularly important in radiographic thoracic imaging (the taking of chest X-rays). In the most common type of chest X-ray, a patient will place his/her chest against a detector and the emitter will be activated to send X-rays through the patient from the posterior-to-anterior direction and into the detector. When the image is captured, a radiologist must then systematically evaluate the image to identify the chest wall, diaphragm, lungs, pleura, mediastinum, etc. To properly identify and analyze matters of medical importance, it is desirable to be able to identify extremely small objects on the image, e.g., details as small as 0.7–2.0 mm near the center of the lungs and 0.3–2.0 mm near their periphery. However, it is difficult for a radiologist to identify objects this small on a two-dimensional image, particularly since some objects may be overlapping and their boundaries may be difficult to accurately discern.

Solutions to the problems described above have not heretofore included significant remote capabilities. In particular, communication networks, such as, the Internet or private networks, have not been used to provide remote services to such medical diagnostic systems. The advantages of remote services, such as, remote monitoring, remote system control, immediate file access from remote locations, remote file storage and archiving, remote resource pooling, remote recording, remote diagnostics, and remote high speed computations have not heretofore been employed to solve the problems discussed above.

Thus, there is a need for a medical diagnostic system which provides for the advantages of remote services and addresses the problems discussed above. In particular, there is a need for stereo radiography including remote control via a network. Further, there is a need for manipulation of imaging systems by skilled operators or physicians in remote locations. Even further, there is a need to be able to make available matters of medical importance in many locations.

SUMMARY OF THE INVENTION

One embodiment of the invention relates to a radiographic imaging system including an X-ray emitter, an X-ray detector, and a network. The X-ray emitter is actuatable to emit an X-ray beam centered about an X-ray beam axis. The X-ray detector has a generally planar configuration and is situated within the path of the X-ray beam to thereby generate an image when the X-ray detector receives the X-ray beam. The network couples at least one of the X-ray emitter and X-ray detector to a remote facility. The network provides the X-ray emitter and the X-ray detector with remote services from the remote facility.

Another embodiment of the invention relates to a method of radiographic imaging including situating a target between an X-ray emitter and an X-ray detector in an imaging system, wherein the X-ray detector is at least substantially planar and the X-ray emitter may be activated to emit an X-ray beam toward the X-ray detector, the X-ray beam being centered about an X-ray beam axis; establishing a communication connection over a network between a remote facility and the imaging system; remotely activating the X-ray emitter to emit the X-ray beam from a first imaging position relative to the X-ray detector, the first imaging position being situated in an imaging plane which is at least substantially parallel to the X-ray detector, thereby obtaining a first image of the target; remotely controlling the movement of any one of the X-ray emitter and X-ray detector to situate the X-ray emitter in a second imaging position relative to the X-ray detector, the second imaging position being situated in the imaging plane; remotely activating the X-ray emitter to emit the X-ray beam from the second imaging position to thereby obtain a second image of the target; and stereoscopically combining the first and second images.

Another embodiment of the invention relates to a radiographic imaging system including an X-ray emitter, an X-ray detector, a target area, and a network. The X-ray emitter is actuatable to emit an X-ray beam centered about an X-ray beam axis. The X-ray detector has a generally planar configuration and is situated within the path of the X-ray beam to thereby generate an image when the X-ray detector receives the X-ray beam. The target area is situated between the X-ray detector and the X-ray emitter, wherein a target to be radiographically imaged may be located. The network couples at least one of the X-ray emitter and X-ray detector to a remote facility. At least one of the X-ray emitter and X-ray detector are automatically movable via operator commands communicated via the network to generate in rapid succession a first and second image of the target area. The first image of the target area is one in which the X-ray emitter is situated at a first imaging position in an imaging plane which is at least substantially parallel to the plane of the X-ray detector. The second image of the target area is one in which the X-ray emitter is situated in a second imaging position in the imaging plane.

Another embodiment of the invention relates to a radiographic imaging system including an X-ray emitter, an X-ray detector, a network, a display, and eyeglasses. The X-ray emitter is actuatable to emit an X-ray beam centered about an X-ray beam axis. The X-ray detector has a generally planar configuration and is situated within the path of the X-ray beam to thereby generate an image when the X-ray detector receives the X-ray beam. The network couples at least one of the X-ray emitter and X-ray detector to a remote facility. At least one of the X-ray emitter and the X-ray detector are movable via operator commands communicated via the network in a plane oriented at least substantially parallel to the plane of the X-ray detector, whereby the X-ray emitter may be activated to generate images from different imaging positions relative to the X-ray detector. The display provides the images from different imaging positions in rapid alternating succession and the eyeglasses have two viewing ports wherein each port alternately obscures the images from different imaging positions in synchronization with the display.

Other principle features and advantages of the present invention will become apparent to those skilled in the art upon review of the following drawings, the detailed description, and the appended claims.

BRIEF DESCRIPTION OF THE DRAWINGS

Preferred exemplary embodiments are described below with reference to the accompanying drawings, wherein like reference numerals denote like elements, and.

DETAILED DESCRIPTION OF THE PREFERRED EMBODIMENT

Figure 1:
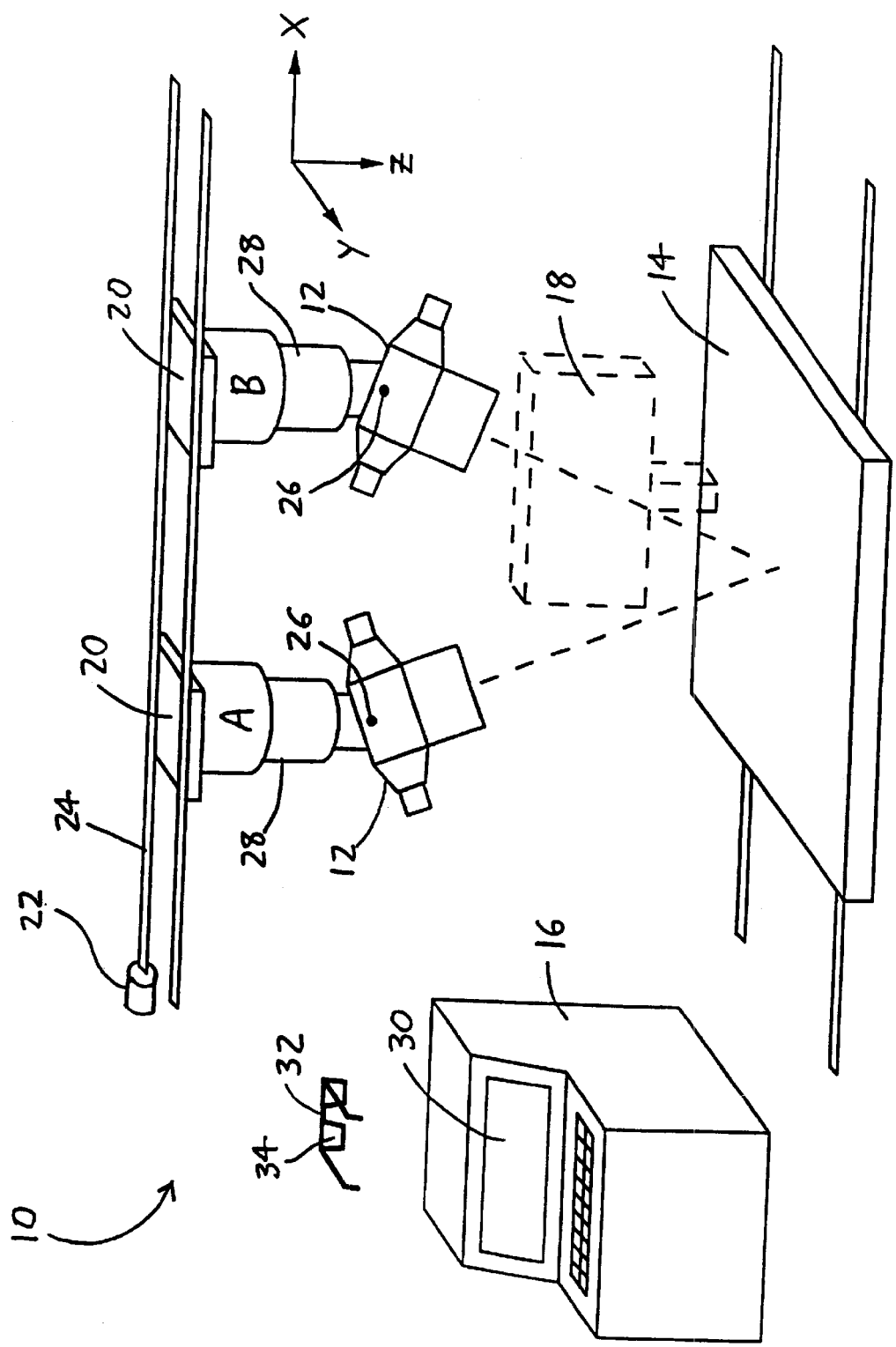
FIG. 1 is a perspective view of an exemplary embodiment of a stereo radiography system in accordance with a preferred embodiment of the invention.

FIG. 1 illustrates a first exemplary embodiment of a stereo radiography system, which is generally designated by the reference numeral 10. The primary components of the illustrated system 10 includes an X-ray emitter 12 and an X-ray detector 14 between which a target to be X-rayed may be situated, and a processing and display station 16 wherein controls for the emitter 12 and detector 14 are provided and at which images of the X-rayed target are displayed. It is noted that the emitter 12 is shown twice in FIG. 1 not because two emitters 12 are required by the inventor, but rather to depict the motion of the emitter 12 from a first imaging position A to a second imaging position B. Each of the foregoing components will now be discussed in turn.

The X-ray emitter 12 is mounted on a trolley 20 which may be actuated (e.g., by actuator 22) to ride on tracks 24 to allow the trolley 20 to translate along a path oriented generally parallel to the plane of the X-ray detector 14, i.e., in the x direction illustrated in the FIG. 1. For reasons that will be discussed in greater detail below, the X-ray emitter 12 is also preferably mounted to the trolley 20 by a pivot 26 which allows the X-ray emitter 12 to be actuated to rotate about an axis parallel to the X-ray detector 14, and perpendicular to the path of translation of the X-ray emitter 12. Thus, where the horizontally oriented X-ray detector 14 is used (i.e., the X-ray detector 14 is in the xy plane), the pivot 26 allows actuation of the X-ray emitter 12 to rotate about the illustrated y axis. Apart from moving in these two degrees of freedom, the X-ray emitter 12 and trolley 20 could be adapted to translate and/or rotate in other dimensions as well. For example, a telescoping column 28 may be provided between the trolley 20 and the X-ray emitter 12 to allow the X-ray emitter 12 to translate in the z direction; the column 28 can be situated on tracks/slides on the trolley 20 to translate in the y direction; additional pivots could be provided to allow rotation of the X-ray emitter 12 about the x and z axes; etc. While these motions enhance the versatility of the invention, they are not required. For purposes of the preferred embodiment, the X-ray emitter 12 need only be able to translate in at least one dimension oriented generally parallel to the plane of the X-ray detector 14, and it is also particularly preferable that the X-ray emitter 12 be able to rotate about at least one axis parallel to the plane of the X-ray detector 14.

Regarding the actuator 22, any number of known servo-motor systems or other actuators may be used to drive the trolley 20 along the tracks 24 and about the pivot 26. In practice, the actuator 22 and tracks 24 may be provided by equipping standard General Electric Medical Systems S3805XT Radiographic Suspension System tracks with VIOLIN and SDC servomotor/controller systems (Elmo Motion Control Ltd., Petach-Tikuva, Israel).

The X-ray detector 14, which has a substantially planar configuration as noted above, is a digital detector rather than an analog detector. It is noted that while the detector 14 is illustrated as being horizontally oriented, as is common where detectors are provided in combination with observation tables, the detector 14 could be provided in a variety of other orientations (as exemplified by the vertically-oriented detector 18 shown in phantom lines in FIG. 1). As will be discussed at greater length below, similarly to the X-ray emitter 12, the X-ray detector 14 may also be adapted to allow it to translate and/or rotate relative to the X-ray emitter 12. As an example, within FIG. 1, the tracks 24 allow the X-ray detector 14 to linearly translate with respect to the X-ray emitter 12. Motion of the X-ray detector 14, if provided, may be in lieu of or in addition to motion of the X-ray emitter 12. If both the X-ray emitter 12 and the X-ray detector 14 are adapted for motion, their translation should preferably occur along parallel paths, and their rotation should preferably occur about parallel axes.

In the foregoing arrangement, a target to be radiographically imaged is situated between the X-ray emitter 12 and the X-ray detector 14 (or 18) so that emitted X-rays pass through the target to strike the X-ray detector, as in standard radiographic imaging systems. A controller (which is not shown but which is preferably included within the processing and display station 16) then translates the X-ray emitter 12 along the tracks 24 by a sufficient distance that images generated by the X-ray emitter 12 and X-ray detector 14 before and after translation will display parallax separation between objects within the images. The translation and imaging steps ideally take place during a time period which is sufficiently short that a patient can comfortably hold his/her breath (preferably no more than six seconds, and more preferably on the order of one second or less). As will be discussed below, the images can then be combined to create a stereoscopic (three-dimensional) view of the target. In general, a stereoscopic image of high resolution may be generated when the angle swept by the X-ray emitter 12 with respect to the midpoint of its sweep on the X-ray detector 14 measures between 3–8 degrees. For a standard SID (source-to-image distance, i.e., the distance between the X-ray emitter 12 and X-ray detector 14) of 180 centimeters, an 8 degree angle corresponds to a translation of approximately 25 centimeters for the X-ray emitter, whereas a 3 degree angle corresponds to a translation of approximately 9.5 cm. Such distances are readily achievable by servomotors of reasonable quality within the timeframe of a patient breath hold.

Once the initial and final images are obtained, they are processed by some form of means for generating a stereoscopic view of the target area from the initial and final images. In the imaging system 10 illustrated in FIG. 1, the processing and display station 16 includes a display screen 30 whereupon the initial and final images are displayed in rapid alternating succession. A pair of eyeglasses 32 are then provided wherein a pair of ports 34 is defined, one for each of a viewer's eyes. The ports 34 are each adapted to rapidly open and close in alternating succession in synchronization with the alternating images on the display screen 30; thus, one of the initial and final images is always viewed through one port 34, and the other of the initial and final images is always viewed through the other port 34. Stereoscopic view generators of this type are known and are provided (for example) by the CrystalEyes system (StereoGraphics Corporation, San Rafael, Calif., USA), wherein the ports 34 of the eyeglasses 32 are liquid crystal displays which allow a viewer's left eye to see only one of the initial and final images and the right eye to see only the other image, with the display screen 30 alternating the initial and final images 120 times per second. As a result, a human viewer effectively perceives the separate images as a single three-dimensional image. Advantageously, the CrystalEyes eyeglasses 32 communicate with the display screen 30 by an infrared signal, and thereby a number of eyeglasses 32 may be worn by a number of viewers simultaneously with complete freedom of movement within 8–10 feet of the processing and display station 16. Other means for stereoscopically combining the separate images can additionally or alternatively be used in place of the CrystalEyes scheme, with almost any such means known to the prior art being suitable for use in the invention. As examples, dual images can be combined using a wide variety of known means whereby each port of a pair of eyeglasses 32 masks one image from view (e.g., as in common red/green "3-D glasses"), and greater numbers of images can be combined by interleaving the images and providing lens arrays or screens which only allow certain portions of certain images to be visible from certain angles.

Because the processing and display station 16 receives and processes images in digital form, locations of objects contained within the images can be compared and their depths within the target may be quantified. If the visual separation angle between the target/detector 14 is known (and it generally will be since the source-to-image distance is generally known or easily measurable, and the distance between the initial and final locations of the X-ray emitter 12 are known), the depths of objects within the target may be readily calculated using standard stereo calculations. This step can be performed, for example, by providing a movable cursor on the display screen 30 whereby viewers can select particular objects, and the processing and display station 16 can then perform the measurements and calculations necessary to display the calculated depths of the selected objects.

As noted above, it is preferable to couple the translation of the X-ray emitter 12 with rotation of the emitter 12 in a plane which is parallel to the path along which the X-ray emitter translates, and also perpendicular to the plane of the X-ray detector 14. Such rotation is desirable so that the X-ray beam may be centered about the same area on the X-ray detector 14 in both the initial and final positions A and B of the X-ray emitter 12 (as illustrated in FIG. 1). This rotation is not absolutely necessary since a suitable stereographic image may be constructed from images taken when the X-ray emitter 12 is simply translated within a plane parallel to the X-ray detector 14. However, the combination of such images will suffer from a reduction in the width of field since each image will contain portions of the target that the other does not, and these areas of the images cannot be stereographically combined.

As also noted above, in lieu of translating the X-ray emitter 12, it is instead possible to translate the X-ray detector 14 and obtain images of the target prior to and after such translation. In this situation, only the detector 14 need be moved and the X-ray emitter 12 can be maintained immobile (or can be rotated so that both of the initial and final images are centered about the same area on the target/detector 14). Since this arrangement merely reverses the relative motion of the X-ray emitter 12 and X-ray detector 14, this allows essentially the same images as when only the emitter 12 is moved.

In further embodiments of the preferred embodiment, both of the X-ray emitter 12 and the X-ray detector 14 may be moved simultaneously in opposite directions to effect the positioning of the emitter 12 with respect to the detector 14. This arrangement can allow the extent of translation and/or rotation of each of the X-ray emitter 12 and/or X-ray detector 14 to be reduced by as much as one-half, thereby requiring lesser time for the emitter 12 and detector 14 to achieve positioning in their initial and final locations. While this is seemingly not very significant, it is nevertheless quite advantageous insofar as the X-ray emitter 12 and/or X-ray detector 14 may be somewhat massive, and lesser ranges in motion can allow the use of lower-priced servo/control systems, lesser delay times between obtaining the initial and final images (and thus lesser time in which a patient must hold his/her breath), and/or gentler acceleration schemes during translation (resulting in lesser oscillation in the X-ray emitter 12 and X-ray detector 14 upon stopping, which is helpful since such oscillation can lead to loss of resolution in the stereoscopic image).

While the X-ray emitter 12 is illustrated as being mounted to the ceiling and the X-ray detector 14 as being mounted to a floor, it should be understood that the X-ray emitter 12 and/or X-ray detector 14 can be mounted in many other arrangements as well. As examples, the X-ray emitter 12 could be mounted to translate along the floor and/or wall, the X-ray detector 14 could translate along a wall and/or ceiling, etc.

Figure 2:
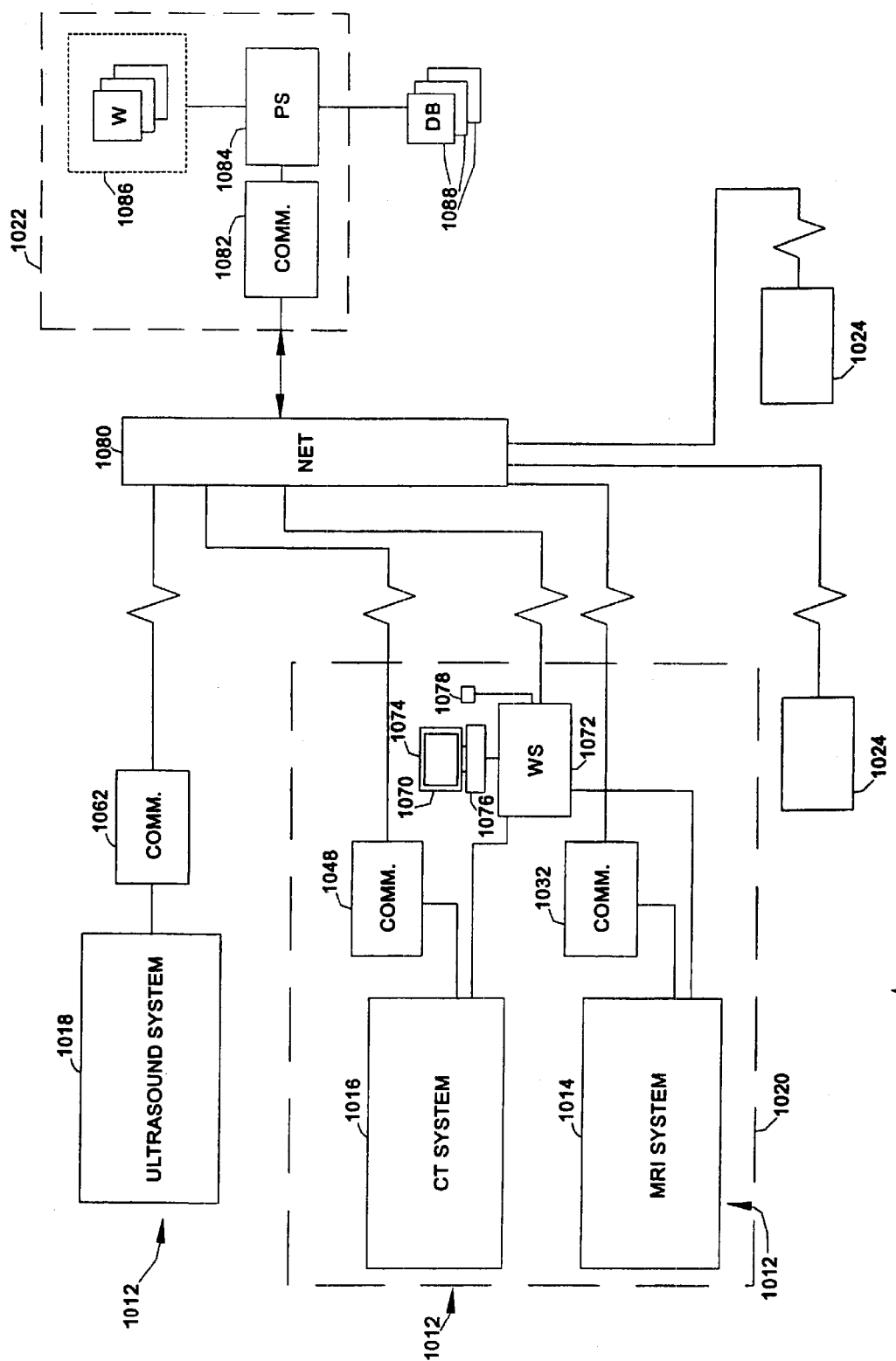
FIG. 2 is a diagrammatical representation of a series of medical diagnostic systems coupled to a service facility via a network connection for providing remote services and data interchange between the diagnostic systems and the service facility.

Referring now to FIG. 2, a service system 1010 is illustrated for providing remote service to a plurality of medical diagnostic systems 1012, including systems such as stereo radiography system 10 described with reference to FIG. 1. In the embodiment illustrated in FIG. 2, the medical diagnostic systems include a magnetic resonance imaging (MRI) system 1014, a computed tomography (CT) system 1016, and an ultrasound imaging system 1018. The diagnostic systems may be positioned in a single location or facility, such as a medical facility 1020, or may be remote from one another as shown in the case of ultrasound system 1018. The diagnostic systems are serviced from a centralized service facility 1022. Moreover, a plurality of field service units 1024 may be coupled in the service system for transmitting service requests, verifying service status, transmitting service data and so forth as described more fully below.

In the exemplary embodiment of FIG. 2, several different system modalities are provided with remote service by the service facility. Remote services include but are not limited to services, such as, remote monitoring, remote system control, immediate file access from remote locations, remote file storage and archiving, remote resource pooling, remote recording, and remote high speed computations. Remote services are provided to a particular modality depending upon the capabilities of the service facility, the types of diagnostic systems subscribing to service contracts with the facility, as well as other factors.

Depending upon the modality of the systems, various subcomponents or subsystems will be included. In the case of MRI system 1014, such systems will generally include a scanner, a control and signal detection circuit, a system controller, and an operator station. MRI system 1014 includes a uniform platform for interactively exchanging service requests, messages and data with service facility 1022 as described more fully below. MRI system 1014 is linked to a communications module 1032, which may be included in a single or separate physical package from MRI system 1014. In a typical system, additional components may be included in system 1014, such as a printer or photographic system for producing reconstructed images based upon data collected from the scanner.

Similarly, CT system 1016 will typically include a scanner, a signal acquisition unit, and a system controller. The scanner detects portions of x-ray radiation directed through a subject of interest. The controller includes circuitry for commanding operation of the scanner and for processing and reconstructing image data based upon the acquired signals. CT system 1016 is linked to a communications module 1048 for transmitting and receiving data for remote services. Moreover, like MRI system 1014, CT system 1016 will generally include a printer or similar device for outputting reconstructed images based upon data collected by the scanner.

In the case of ultrasound system 1018, such systems will generally include a scanner and data processing unit and a system controller. Ultrasound system 1018 is coupled to a communications module 1062 for transmitting service requests, messages and data between ultrasound system 1018 and service facility 1022.

Although reference is made herein generally to "scanners" in diagnostic systems, that term should be understood to include medical diagnostic data acquisition equipment generally, not limited to image data acquisition, as well as to picture archiving communications and retrieval systems, image management systems, facility or institution management systems, viewing systems and the like, in the field of medical diagnostics.

Where more than one medical diagnostic system is provided in a single facility or location, as indicated in the case of MRI and CT systems 1014 and 1016 in FIG. 2, these may be coupled to a management station 1070, such as in a radiology department of a hospital or clinic. The management station may be linked directly to controllers for the various diagnostic systems. The management system may include a computer workstation or personal computer 1072 coupled to the system controllers in an intranet configuration, in a file sharing configuration, a client/server arrangement, or in any other suitable manner. Moreover, management station 1070 will typically include a monitor 1074 for viewing system operational parameters, analyzing system utilization, and exchanging service requests and data between the facility 1020 and the service facility 1022. Input devices, such as a standard computer keyboard 1076 and mouse 1078, may also be provided to facilitate the user interface.

It should be noted that, alternatively, the management system, or other diagnostic system components, may be "stand-alone" or not coupled directly to a diagnostic system. In such cases, the service platform described herein, and some or all of the service functionality nevertheless be provided on the management system. Similarly, in certain applications, a diagnostic system may consist of a stand-alone or networked picture archiving communications and retrieval system or a viewing station provided with some or all of the functionality described herein.

The communication modules mentioned above, as well as workstation 1072 and field service units 1024 may be linked to service facility 1022 via a remote access network 1080. For this purpose, any suitable network connection may be employed. Presently preferred network configurations include both proprietary or dedicated networks, as well as open networks, such as the Internet. Data may be exchanged between the diagnostic systems, field service units, and remote service facility 1022 in any suitable format, such as in accordance with the Internet Protocol (IP), the Transmission Control Protocol (TCP), or other known protocols. Moreover, certain of the data may be transmitted or formatted via markup languages such as the HyperText Markup Language (HTML), or other standard languages. The presently preferred interface structures and communications components are described in greater detail below.

Within service facility 1022, messages, service requests and data are received by communication components as indicated generally at reference numeral 1082. Components 1082 transmit the service data to a service center processing system, represented generally at reference numeral 1084 in FIG. 2. The processing system manages the receipt, handling and transmission of service data to and from the service facility. In general, processing system 1084 may include one or a plurality of computers, as well as dedicated hardware or software servers for processing the various service requests and for receiving and transmitting the service data as described more fully below.

Service facility 1022 also includes a bank of operator workstations 1086 which may be staffed by personnel who address the service requests and provide off and online service to the diagnostic systems in response to the service requests. Also, processing system 1084 may be linked to a system of databases or other processing systems 1088 at or remote from the service facility 1022. Such databases and processing systems may include extensive database information on operating parameters, service histories, and so forth, both for particular subscribing scanners, as well as for extended populations of diagnostic equipment.

Figure 3:
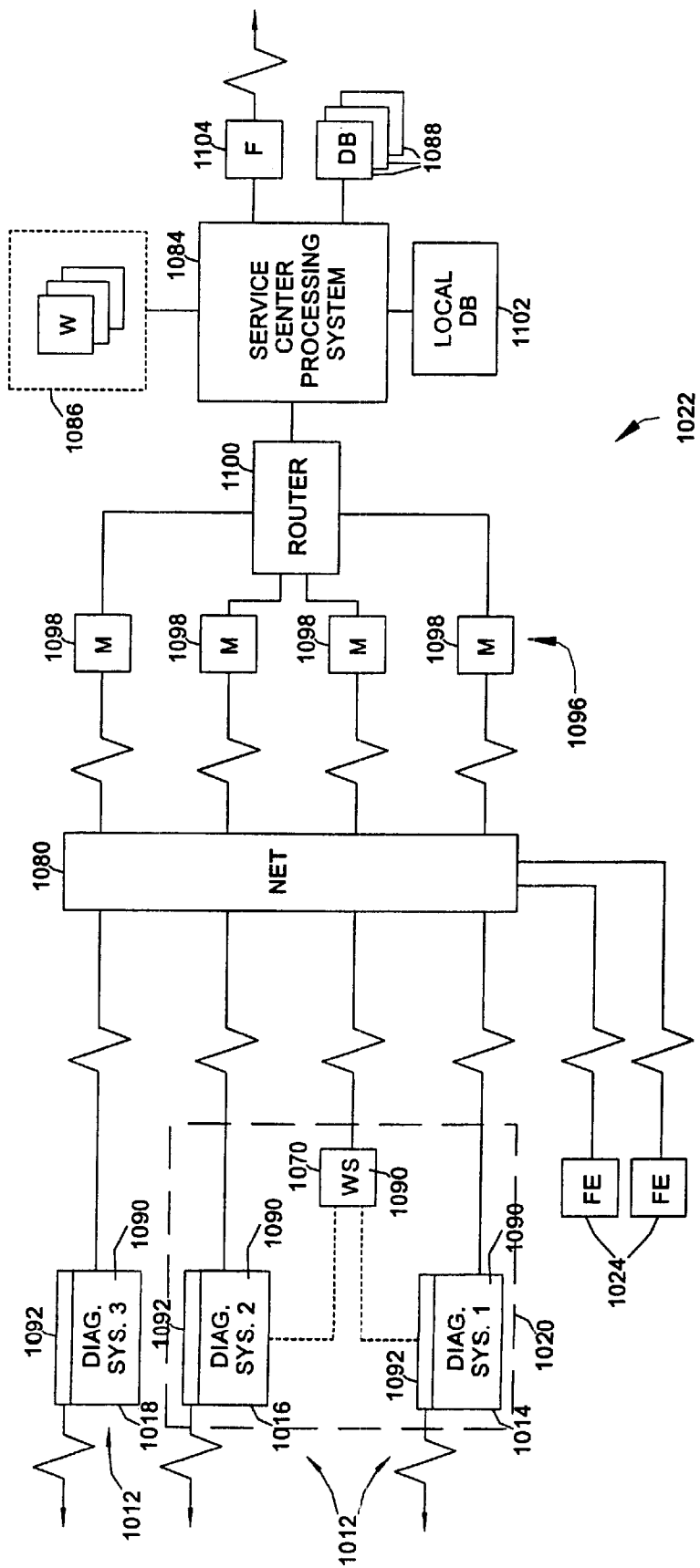
FIG. 3 is a block diagram of the systems shown in FIG. 2 illustrating certain functional components of the diagnostic systems and the service facility.

FIG. 3 is a block diagram illustrating the foregoing system components in a functional view. As shown in FIG. 3, the field service units 1024 and the diagnostic systems 1012 can be linked to the service facility 1022 via a network connection as illustrated generally at reference numeral 1080. Within each diagnostic system 1012, a uniform service platform 1090 is provided.

Platform 1090, which is described in greater detail below with particular reference to FIG. 4, includes hardware, firmware, and software components adapted for composing service requests, transmitting and receiving service data, establishing network connections and managing financial or subscriber arrangements between diagnostic systems and the service facility. Moreover, the platforms provide a uniform graphical user interface at each diagnostic system, which can be adapted to various system modalities to facilitate interaction of clinicians and radiologists with the various diagnostic systems for service functions. The platforms enable the scanner designer to interface directly with the control circuitry of the individual scanners, as well as with memory devices at the scanners, to access image, log and similar files needed for rendering requested or subscribed services. Where a management station 1070 is provided, a similar uniform platform is preferably loaded on the management station to facilitate direct interfacing between the management station and the service facility. In addition to the uniform service platform 1090, each diagnostic system is preferably provided with an alternative communications module 1092, such as a facsimile transmission module for sending and receiving facsimile messages between the scanner and remote service facilities.

Messages and data transmitted between the diagnostic systems and the service facility traverse a security barrier or "firewall" contained within processing system 1084 as discussed below, which prevents unauthorized access to the service facility in a manner generally known in the art. A modem rack 1096, including a series of modems 1098, receives the incoming data, and transmits outgoing data through a router 1100 which manages data traffic between the modems and the service center processing system 1084.

In the diagram of FIG. 3, operator workstations 1086 are coupled to the processing system, as are remote databases or computers 1088. In addition, at least one local service database 1102 is provided for verifying license and contract arrangements, storing service record files, log files, and so forth. Moreover, one or more communication modules 1104 are linked to processing system 1084 to send and receive facsimile transmissions between the service facility and the diagnostic systems or field service units.

Figure 4:
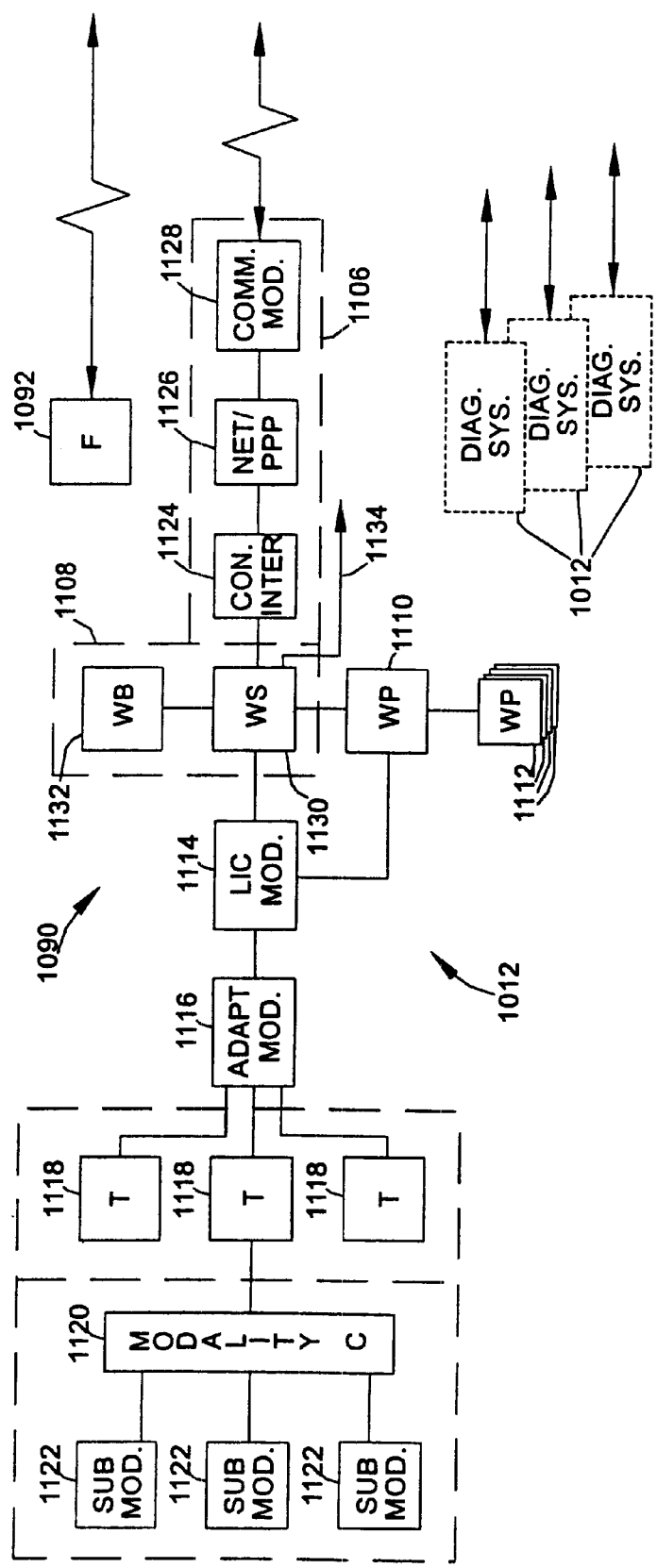
FIG. 4 is a block diagram of certain functional components within a diagnostic system of the type shown in FIGS. 2 and 3 for facilitating interactive remote servicing of the diagnostic system.

FIG. 4 illustrates diagrammatically the various functional components comprising the uniform service platform 1090 within each diagnostic system 1012. As shown in FIG. 4, the uniform platform includes a device connectivity module 1106, as well as a network connectivity module 1108. Network connectivity module 1108 accesses a main web page 1110 which, as mentioned above, is preferably a markup language page, such as an HTML page displayed for the system user on a monitor at the diagnostic system. Main web page 1110 is preferably accessible from a normal operating page in which the user will configure examination requests, view the results of examinations, and so forth such as via an on-screen icon. Through main web page 1110, a series of additional web pages 1112 are accessible. Such web pages permit remote service requests to be composed and transmitted to the remote service facility, and facilitate the exchange of other messages, reports, software, protocols, and so forth as described more fully below.

It should be noted that as used herein the term "page" includes a user interface screen or similar arrangement which can be viewed by a user of the diagnostic system, such as screens providing graphical or textual representations of data, messages, reports and so forth. Moreover, such pages may be defined by a markup language or a programming language such as Java, perl, java script, or any other suitable language.

Network connectivity module 1108 is coupled to a license module 1114 for verifying the status of license, fee or contractual subscriptions between the diagnostic system and the service facility. As used herein, the term "subscription" should be understood to include various arrangements, contractual, commercial or otherwise for the provision of services, information, software, and the like, both accompanies with or without payment of a fee. Moreover, the particular arrangements manages by systems as described below may include several different types of subscriptions, including time-expiring arrangements, one-time fee arrangements, and so-called "pay per use" arrangements, to mention but a few.

License module 1114 is, in turn, coupled to one or more adapter utilities 1116 for interfacing the browser, server, and communications components with modality interface tools 1118. In a presently preferred configuration, several such interface tools are provided for exchanging data between the system scanner and the service platform. For example, modality interface tools 1118 may include applets or servlets for building modality-specific applications, as well as configuration templates, graphical user interface customization code, and so forth. Adapters 1116 may interact with such components, or directly with a modality controller 1120 which is coupled to modality-specific subcomponents 1122.

The modality controller 1120 and modality-specific subcomponents 1122 will typically include a preconfigured processor or computer for executing examinations, and memory circuitry for storing image data files, log files, error files, and so forth. Adapter 1116 may interface with such circuitry to convert the stored data to and from desired protocols, such as between the HyperText Transfer Protocol (HTTP) and DICOM, a medical imaging standard for data presentation. Moreover, transfer of files and data as described below may be performed via any suitable protocol, such as a file transfer protocol (FTP) or other network protocol.

In the illustrated embodiment, device connectivity module 1106 includes several components for providing data exchange between the diagnostic system and the remote service facility. In particular, a connectivity service module 1124 provides for interfacing with network connectivity module 1108. A Point-to-Point Protocol (PPP) module 1126 is also provided for transmitting Internet Protocol (IP) packets over remote communication connections. Finally, a modem 1128 is provided for receiving and transmitting data between the diagnostic system and the remote service facility. As will be appreciated by those skilled in the art, various other network protocols and components may be employed within device connectivity module 1106 for facilitating such data exchange.

Network connectivity module 1108 preferably includes a server 1130 and a browser 1132. Server 1130 facilitates data exchange between the diagnostic system and the service facility, and permits a series of web pages 1110 and 1112 to be viewed via browser 1132. In a presently preferred embodiment, server 1130 and browser 1132 support HTTP applications and the browser supports java applications. Other servers and browsers, or similar software packages may, of course, be employed for exchanging data, service requests, messages, and software between the diagnostic system, the operator and the remote service facility. Finally, a direct network connection 1134 may be provided between server 1130 and an operator workstation, such as management station 1070 within the medical facility (see FIGS. 2 and 3).

In a present embodiment, the components comprising network connectivity module may be configured via an application stored as part of the uniform platform. In particular, a Java application licensed to a service engineer enables the engineer to configure the device connectivity at the diagnostic system to permit it to connect with the service facility.

Figure 5:
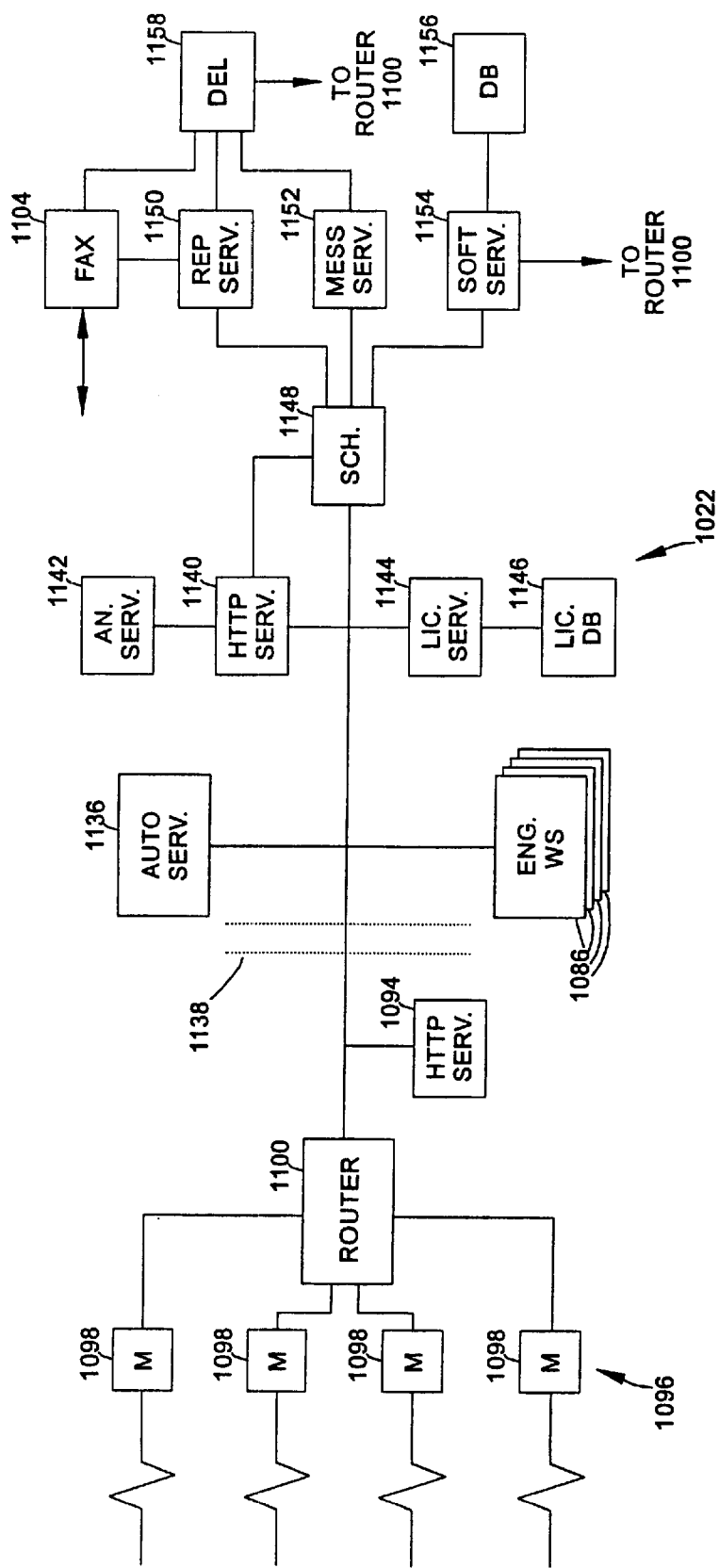
FIG. 5 is a block diagram of certain of the functional components of the service facility illustrated in FIGS. 2 and 3 for rendering interactive remote service to a plurality of medical diagnostic systems.

FIG. 5 illustrates exemplary functional components for service facility 1022. As indicated above, service facility 1022 includes a modem rack 1096 comprising a plurality of modems 1098 coupled to a router 1100 for coordinating data communications with the service facility. An HTTP service server 1094 receives and directs incoming and outgoing transactions with the facility. Server 1094 is coupled to the other components of the facility through a firewall 1138 for system security. Operator workstations 1086 are coupled to the port manager for handling service requests and transmitting messages and reports in response to such requests.

An automated service unit 1136 may also be included in the service facility for automatically responding to certain service requests, sweeping subscribing diagnostic systems for operational parameter data, and so forth, as described below. In a presently preferred embodiment, the automated service unit may operate independently of or in conjunction with the interactive service components comprising processing system 1084. It should be noted that other network or communications schemes may be provided for enabling the service facility to communicate and exchange data and messages with diagnostic systems and remote service units, such as systems including outside Internet service providers (ISP's), virtual private networks (VPN's) and so forth.

Behind firewall 1138, an HTTP application server 1140 coordinates handling of service requests, messaging, reporting, software transfers and so forth. Other servers may be coupled to HTTP server 1140, such as service analysis servers 1142 configured to address specific types of service requests, as described more fully below. In the illustrated embodiment, processing system 1084 also includes a license server 1144 which is coupled to a license database 1146 for storing, updating and verifying the status of diagnostic system service subscriptions. Alternatively, where desired, license server 1144 may be placed outside of fire wall 1138 to verify subscription status prior to admission to the service facility.

Handling of service requests, messaging, and reporting is further coordinated by a scheduler module 1148 coupled to HTTP server 1140. Scheduler module 1148 coordinates activities of other servers comprising the processing system, such as a report server 1150, a message server 1152, and a software download server 1154. As will be appreciated by those skilled in the art, servers 1150, 1152 and 1154 are coupled to memory devices (not shown) for storing data such as addresses, log files, message and report files, applications software, and so forth. In particular, as illustrated in FIG. 5, software server 1154 is coupled via one or more data channels to a storage device 1156 for containing transmittable software packages which may be sent directly to the diagnostic systems, accessed by the diagnostic systems, or supplied on pay-per-use or purchase basis. Message and report servers 1152 and 1150 are further coupled, along with communications module 1104, to a delivery handling module 1158, which is configured to receive outgoing messages, insure proper connectivity with diagnostic systems, and coordinate transmission of the messages.

In a presently preferred embodiment, the foregoing functional circuitry may be configured as hardware, firmware, or software on any appropriate computer platform. For example, the functional circuitry of the diagnostic systems may be programmed as appropriate code in a personnel computer or workstation either incorporated entirely in or added to the system scanner. The functional circuitry of the service facility may include additional personal computers or workstations, in addition to a main frame computer in which one or more of the servers, the scheduler, and so forth, are configured. Finally, the field service units may comprise personal computers or laptop computers of any suitable processor platform. It should also be noted that the foregoing functional circuitry may be adapted in a variety of manners for executing the functions described herein. In general, the functional circuitry facilitates the exchange of remote service data between the diagnostic systems and a remote service facility, which is preferably implemented in an interactive manner to provide regular updates to the diagnostic systems of service activities.

As described above, both the diagnostic systems and the field service units preferably facilitate interfacing between a variety of diagnostic system modalities and the remote service facility via a series of interactive user-viewable pages. Exemplary pages include capabilities of providing interactive information, composing service requests, selecting and transferring messages, reports and diagnostic system software, and so forth. Pages facilitate the interaction and use of remote services, such as, remote monitoring, remote system control, immediate file access from remote locations, remote file storage and archiving, remote resource pooling, remote recording, and remote high speed computations.

The user can access specific documents described in text areas of the pages by selection of all or a portion of the text describing the documents. In the presently preferred embodiment, the accessed documents may be stored in local memory devices within the diagnostic system, or selection of the text may result in loading of a uniform resource locator (URL) for accessing a remote computer or server via a network link.

Advantageously, service system 1010 (FIG. 2) provides remote services, such as, remote control, remote diagnostics, remote servicing, and remote file transfer and storage. Advantageously, service system 1010 (FIG. 2) allows system 10 to be controlled from a remote location. As such, specially skilled system operators or physicians may operate system 10 without either the physician travelling to the patient or the patient travelling to the physician. In non-medical applications, remote services also provides advantages for the control and operation of system 10.

Service system 1010 also allows system 10 to be serviced by a remote facility. As such, calibration, service diagnosis, software upgrades, and other service operations are available. Stereo radiography aids in the identification of extremely small objects, overlapping objects, and the like in the operation of imaging systems. Service system 1010 provides system 10 with the ability of remote review and analysis of stereo radiographic images via remote file transfer and storage.

While the embodiments illustrated in the Figures and described above are presently preferred, it should be understood that the embodiments are offered by way of example only. Other embodiments may include other remote services, such as, remote file storage of radiographic images, remote servicing of radiographic imaging equipment, remote diagnostics of radiographic imaging systems, and other services which are available through a remote facility. The invention is not limited to a particular embodiment, but extends to various modifications, combinations, and permutations that nevertheless fall within the scope and spirit of the appended claims.

What is claimed is:

1. A method of radiographic imaging comprising:
   situating a target between an X-ray emitter and an X-ray detector in an imaging system, wherein the X-ray detector is at least substantially planar and the X-ray emitter may be activated to emit an X-ray beam toward the X-ray detector, the X-ray beam being centered about an X-ray beam axis;
   establishing a communication connection over a network between a remote facility and the imaging system;
   remotely activating the X-ray emitter to emit the X-ray beam from a first imaging position relative to the X-ray detector, the first imaging position being situated in an imaging plane which is at least substantially parallel to the X-ray detector, thereby obtaining a first image of the target;
   remotely controlling the movement of any one of X-ray detector to situate the X-ray emitter in a second imaging position relative to the X-ray detector, the second imaging position being situated in the imaging plane;
   remotely activating the X-ray emitter to emit the X-ray beam from the second imaging position to thereby obtain a second image of the target; and
   stereoscopically combining the first and second images.

2. The method of claim 1, wherein the step of remotely controlling the movement of any one of the X-ray emitter and X-ray detector comprises holding immobile the X-ray detector is held immobile and the X-ray emitter is moved.

3. The method of claim 1, wherein the step of remotely controlling the movement of any one of the X-ray emitter and X-ray detector comprises holding immobile the X-ray emitter and X-ray detector.

4. The method of claim 1, wherein the step of remotely controlling the movement of any one of the X-ray emitter and X-ray detector comprises moving both the X-ray emitter and the X-ray detector.

5. The method of claim 4, wherein the step of remotely controlling the movement of any one of the X-ray emitter and X-ray detector comprises translating the X-ray emitter and the X-ray detector along parallel and opposite paths.

6. The method of claim 1, wherein the step of stereoscopically combining the first and second images includes the steps of:
   alternately displaying the first and second images in rapid succession, and
   simultaneously alternately obscuring the view of the first and second images from each of a viewer's right and left eyes.

7. The method of claim 1, wherein the X-ray beam axis is oriented at different angles with respect to the X-ray detector in the first and second imaging positions.

8. The method of claim 7, wherein the X-ray beam axis when the X-ray emitter is at the first imaging position and the X-ray beam axis when the X-ray emitter is at the second imaging position coincide with the same area on the X-ray detector.

9. The method of claim 7, wherein the X-ray beam axis when the X-ray emitter is at the first imaging position intersects the X-ray beam axis when the X-ray emitter is at the second imaging position.

10. The method of claim 9, wherein the intersection of the X-ray beam axes is situated at least as distantly away from the X-ray emitter as the X-ray detector.

11. The method of claim 7, wherein the X-ray beam axis at the first imaging position is oriented at an angle with respect to the X-ray beam axis at the second position, this angle being greater than 0 degrees and less than 10 degrees.

12. The method of claim 1, further comprising the steps of:
   a) measuring the location of the X-ray emitter at the first imaging position;
   b) measuring the location of the X-ray emitter at the second imaging position;
   c) measuring distances between objects contained in the first image;
   d) measuring distances between objects contained in the second image;
   e) utilizing the measured locations and distances of steps a.–d. to determine the relative depths of objects in the first and second images.

13. A radiographic imaging system comprising:
   an X-ray emitter which is actuatable to emit an X-ray beam centered about an X-ray beam axis;
   an X-ray detector having a generally planar configuration, the X-ray detector being situated within the path of the X-ray beam to thereby generate an image when the X-ray detector receives the X-ray beam;
   a target area situated between the X-ray detector and the X-ray emitter, wherein a target to be radiographically imaged may be located;
   a network, the network coupling at least one of the X-ray emitter and X-ray detector to a remote facility;
   wherein at least one of the X-ray emitter and X-ray detector are automatically movable via operator commands communicated via the network to generate in rapid succession:
      a first image of the target area, wherein the X-ray emitter is situated at a first imaging position in an imaging plane which is at least substantially parallel to the plane of the X-ray detector, and
      a second image of the target area, wherein the X-ray emitter is situated in a second imaging position in the imaging plane.

14. The radiographic imaging system of claim 13, further comprising an emitter actuator operatively associated with the X-ray emitter, the emitter actuator being actuatable to move the X-ray emitter across a path within the imaging plane.

15. The radiographic imaging system of claim 13, further comprising a detector actuator operatively associated with the X-ray detector, the detector actuator being actuatable to move the X-ray detector across a path parallel to the imaging plane.

16. The radiographic imaging system of claim 15, further comprising an emitter actuator operatively associated with the X-ray emitter, the emitter actuator being actuatable to move the X-ray emitter across a path within the imaging plane.

17. The radiographic imaging system of claim 13, wherein:
   the X-ray beam axis is at a first angle with respect to the plane of the X-ray detector when the X-ray emitter is at the first imaging position, and
   the X-ray beam axis is at a second angle with respect to the plane of the X-ray detector when the X-ray emitter is at the second imaging position.

18. The radiographic imaging system of claim 13, further comprising means for generating a stereoscopic view of the target area from the first and second images.

19. The radiographic imaging system of claim 18, wherein the means for generating a stereoscopic view of the target area includes:

a screen whereupon the first and second images are displayed, and eyeglasses having two viewing ports wherein each port obscures a respective one of the first and second images from a viewer's eyes.

20. A radiographic imaging system comprising:

an X-ray emitter which is actuatable to emit an X-ray beam centered about an X-ray beam axis;

an X-ray detector having a generally planar configuration, the X-ray detector being situated within the path of the X-ray beam to thereby generate an image when the X-ray detector receives the X-ray beam;

a network, the network coupling at least one of the X-ray emitter and X-ray detector to a remote facility;

wherein at least one of the X-ray emitter and the X-ray detector are movable via operator commands communicated via the network in a plane oriented at least substantially parallel to the plane of the X-ray detector, whereby the X-ray emitter may be activated to generate images from different imaging positions relative to the X-ray detector;

a display providing the images from different imaging positions in rapid alternating succession, and eyeglasses having two viewing ports wherein each port alternately obscures the images from different imaging positions in synchronization with the display.

* * * * *

UNITED STATES PATENT AND TRADEMARK OFFICE
CERTIFICATE OF CORRECTION

PATENT NO.    : 6,359,961 B1
DATED         : March 19, 2002
INVENTOR(S)   : Richard Aufrichtig et al.

It is certified that error appears in the above-identified patent and that said Letters Patent is hereby corrected as shown below:

<u>Column 10,</u>
Lines 5-6, delete "accom-panies" and substitute -- accompanied --;
Line 7, delete "manages" and substitute -- managed --;

<u>Column 12,</u>
Line 1, delete "personnel" and substitute -- personal --;

<u>Column 13,</u>
Line 17, after "one" delete "of".
Line 28, delete "is held immobile";
Line 28, after "and" insert -- moving --;
Line 28, after "emitter" delete "is moved".

Signed and Sealed this

Twenty-fourth Day of September, 2002

Attest:

JAMES E. ROGAN
Attesting Officer     Director of the United States Patent and Trademark Office